United States Patent
Deno et al.

(10) Patent No.: US 8,948,476 B2
(45) Date of Patent: Feb. 3, 2015

(54) DETERMINATION OF CARDIAC GEOMETRY RESPONSIVE TO DOPPLER BASED IMAGING OF BLOOD FLOW CHARACTERISTICS

(75) Inventors: D. Curtis Deno, Andover, MN (US); Anthony D. Hill, Minneapolis, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 865 days.

(21) Appl. No.: 12/972,723

(22) Filed: Dec. 20, 2010

(65) Prior Publication Data

US 2012/0155723 A1 Jun. 21, 2012

(51) Int. Cl.
*G06K 9/00* (2006.01)
*G06T 7/00* (2006.01)

(52) U.S. Cl.
CPC ..... *G06T 7/0044* (2013.01); *G06T 2207/10132* (2013.01); *G06T 2207/30104* (2013.01); *G06T 2207/30204* (2013.01)
USPC .......................................... 382/128; 600/101

(58) Field of Classification Search
CPC .. G06T 7/0012; G06T 17/00; A61B 19/5244; A61B 19/5225
USPC .......... 382/128–132, 195; 600/101, 109, 112, 600/114, 117–118, 139, 145, 173, 409, 600/415–416, 420, 424, 426, 427, 434, 454, 600/509, 512, 562, 587; 606/1, 45, 130, 606/159; 700/57, 245, 266; 702/19, 50; 703/2, 6, 11; 128/920, 922; 436/172; 345/424; 348/46, 163; 356/28, 39, 356/244–246, 319, 336–338, 365, 419, 356/432–444; 250/573
See application file for complete search history.

(56) References Cited

U.S. PATENT DOCUMENTS

| | | | |
|---|---|---|---|
| 4,951,682 | A | 8/1990 | Petre |
| 5,279,299 | A | 1/1994 | Imran |
| 5,295,484 | A | 3/1994 | Marcus |
| 5,297,549 | A | 3/1994 | Beatty |
| 5,341,807 | A | 8/1994 | Nardella |
| 5,409,000 | A | 4/1995 | Imran |

(Continued)

FOREIGN PATENT DOCUMENTS

WO 00/07501 2/2000

OTHER PUBLICATIONS

International Search Report and Written Opinion, PCT/US2011/063591 Apr. 16, 2012.

(Continued)

*Primary Examiner* — Hadi Akhavannik
(74) *Attorney, Agent, or Firm* — Dykema Gossett PLLC (57) ABSTRACT

A system and method for identifying a location of a physical structure in a body is provided. The system includes an electronic control unit configured to register a first image of a portion of the body in a three-dimensional coordinate system. The electronic control unit is further configured to identify the location of the physical structure in the three-dimensional coordinate system responsive to flow of a fluid shown in the image. The fluid may comprise blood. In one embodiment, the electronic control unit is further configured to generate a second image, such as a three dimensional model, incorporating a representation of the physical structure within a larger physical environment in the three-dimensional coordinate system.

23 Claims, 7 Drawing Sheets

(56) References Cited

U.S. PATENT DOCUMENTS

| | | | |
|---|---|---|---|
| 5,447,529 | A | 9/1995 | Marchlinski |
| 5,462,545 | A | 10/1995 | Wang et al. |
| 5,546,940 | A | 8/1996 | Panescu |
| 5,562,721 | A | 10/1996 | Marchlinski |
| 5,643,255 | A | 7/1997 | Organ |
| 5,662,108 | A | 9/1997 | Budd |
| 5,673,704 | A | 10/1997 | Marchlinski |
| 5,713,946 | A | 2/1998 | Ben-Haim |
| 5,817,022 | A | 10/1998 | Vesely |
| 5,823,955 | A | 10/1998 | Kuck |
| 5,836,875 | A | 11/1998 | Webster, Jr. |
| 5,836,990 | A | 11/1998 | Li |
| 5,904,653 | A * | 5/1999 | Hatfield et al. ............. 600/454 |
| 5,921,923 | A | 7/1999 | Kuck |
| 5,944,712 | A | 8/1999 | Frassica |
| 5,957,842 | A | 9/1999 | Littmann |
| 5,999,840 | A * | 12/1999 | Grimson et al. ............. 600/424 |
| 6,091,995 | A | 7/2000 | Ingle |
| 6,139,498 | A * | 10/2000 | Katsman et al. ............. 600/443 |
| 6,200,314 | B1 | 3/2001 | Sherman |
| 6,216,027 | B1 | 4/2001 | Willis |
| 6,235,018 | B1 | 5/2001 | LePivert |
| 6,289,239 | B1 | 9/2001 | Panescu |
| 6,304,776 | B1 | 10/2001 | Muntermann |
| 6,556,695 | B1 | 4/2003 | Packer |
| 6,895,267 | B2 | 5/2005 | Panescu |
| 6,918,906 | B2 * | 7/2005 | Long ............................. 606/41 |
| 7,263,397 | B2 | 8/2007 | Hauck |
| 7,505,810 | B2 * | 3/2009 | Harlev et al. ............... 600/509 |
| 8,041,413 | B2 | 10/2011 | Barbagli |
| 8,213,693 | B1 | 7/2012 | Li |
| 2002/0151793 | A1 | 10/2002 | Geiser et al. ............... 600/450 |
| 2002/0188194 | A1 | 12/2002 | Cosman |
| 2003/0013958 | A1 | 1/2003 | Govari et al. |
| 2003/0063781 | A1 | 4/2003 | Philomin |
| 2003/0065271 | A1 | 4/2003 | Khoury |
| 2003/0093067 | A1 | 5/2003 | Panescu |
| 2003/0130576 | A1 | 7/2003 | Seeley |
| 2003/0163176 | A1 | 8/2003 | Bae |
| 2003/0163178 | A1 | 8/2003 | Davison |
| 2004/0078036 | A1 * | 4/2004 | Keidar ............................. 606/41 |
| 2004/0097805 | A1 | 5/2004 | Verard et al. |
| 2004/0142485 | A1 | 7/2004 | Flower et al. |
| 2004/0220471 | A1 | 11/2004 | Schwartz |
| 2005/0065434 | A1 | 3/2005 | Bavaro |
| 2005/0203394 | A1 | 9/2005 | Hauck |
| 2005/0246130 | A1 | 11/2005 | Spicer |
| 2007/0027392 | A1 | 2/2007 | Schwartz |
| 2007/0073179 | A1 | 3/2007 | Afonso |
| 2007/0255136 | A1 * | 11/2007 | Kristofferson et al. ........ 600/437 |
| 2007/0299353 | A1 | 12/2007 | Harlev |
| 2008/0085043 | A1 * | 4/2008 | Watanabe et al. ............. 382/131 |
| 2008/0137927 | A1 | 6/2008 | Altmann et al. |
| 2008/0177183 | A1 | 7/2008 | Courtney |
| 2008/0221425 | A1 | 9/2008 | Olson |
| 2008/0221440 | A1 * | 9/2008 | Iddan et al. ................... 600/424 |
| 2008/0249395 | A1 | 10/2008 | Shachar et al. |
| 2008/0300589 | A1 * | 12/2008 | Paul et al. ....................... 606/34 |
| 2009/0107230 | A1 | 4/2009 | Okcay et al. |
| 2009/0177089 | A1 * | 7/2009 | Govari et al. ................ 600/453 |
| 2009/0264777 | A1 * | 10/2009 | Markowitz et al. ........... 600/506 |
| 2009/0275827 | A1 * | 11/2009 | Aiken et al. ................. 600/424 |
| 2009/0292206 | A1 * | 11/2009 | Sato ............................. 600/443 |
| 2009/0292209 | A1 | 11/2009 | Hadjicostis |
| 2010/0099991 | A1 * | 4/2010 | Snyder ......................... 600/454 |
| 2010/0165672 | A1 * | 7/2010 | Li et al. ....................... 363/21.16 |
| 2010/0168569 | A1 | 7/2010 | Sliwa |
| 2010/0168572 | A1 | 7/2010 | Sliwa |
| 2010/0172554 | A1 * | 7/2010 | Kassab et al. ................. 382/128 |
| 2010/0312095 | A1 * | 12/2010 | Jenkins et al. ................ 600/411 |
| 2010/0312096 | A1 * | 12/2010 | Guttman et al. .............. 600/411 |
| 2011/0123088 | A1 * | 5/2011 | Sebok ............................ 382/132 |
| 2011/0125150 | A1 * | 5/2011 | Deno et al. ..................... 606/34 |
| 2011/0142316 | A1 * | 6/2011 | Wang et al. ................... 382/131 |
| 2011/0224655 | A1 * | 9/2011 | Asirvatham et al. ............. 606/1 |
| 2011/0230896 | A1 * | 9/2011 | Wallace et al. ............... 606/130 |
| 2011/0319765 | A1 * | 12/2011 | Gertner et al. ................ 600/453 |
| 2012/0095357 | A1 * | 4/2012 | Tran ............................. 600/509 |
| 2012/0158011 | A1 * | 6/2012 | Sandhu et al. ............... 606/130 |
| 2012/0165672 | A1 * | 6/2012 | Hill et al. ..................... 600/443 |
| 2012/0172724 | A1 | 7/2012 | Hill |
| 2013/0226169 | A1 * | 8/2013 | Miller et al. ................... 606/34 |
| 2013/0310674 | A1 * | 11/2013 | Deno et al. ................... 600/374 |

OTHER PUBLICATIONS

Title: 3D SLICER Citation: 3D SLICER "Modules: Fiducials—Documentation—3.2" (2008).

Bar-Itzhack Y.; "New Method for Extracting the Quaternion from a Rotation Matrix"; J. Guidance, vol. 23, No. 6, Engineering Notes; Reference pp. 1085-1087; Publication Date: Nov. 2000.

Cao, Hong; "FEM Analysis of Predicting Electrode-Myocardium Contact from RF Cardiac Catheter Ablation System Impedance"; IEEE Transactions on Biomedical Engineering, vol. 49, No. 6; Reference pp. 520-526; Publication Date: Jun. 2002.

Cao, Hong; "Using Electrical Impedance to Predict Catheter-Endocardial Contact during RF Cardiac Ablation"; IEEE Transacrions on Biomedical Engineering, vol. 49, No. 3; Reference pp. 247-253; Publication Date: Mar. 2002.

Cinca, Juan: "Changes in Myocardial Electrical Impedance Induced by Coronary Artery Occlusion in Pigs with and without Preconditioning"; Circulation; Publication Date: Nov. 1997.

del Rio, Carlos L.; "Early time course of myocardial electrical impedance during acute coronary artery occlusion in pigs, dogs, and humans": Citation: Journal of Applied Physiology, vol. 99; Reference pp. 1576-1581 Publication Date: Jun. 15, 2005.

Fallert, MA; "Myocardial electrical impedance mapping of ischemic sheep hearts and healing aneurysms"; Citation: Circulation, vol. 67, No. 1; Reference pp. 199-207; Publication Date: Jan. 1993.

Fitzpatrick, Michael J; "Handbook of medical imaging (vol. 2, Medical image processing and analysis" SPIE—The international society for optical engineering; Reference pp. 451-514; Publication Date: Jun. 2000.

Gepstein, Lior; "A novel method for nonfluoroscopio catheter-based electroanatomical mapping of the heart"; Circulation; Publication Date Mar. 1997.

Haines, DE; "Observations on electrode-tissue interface temperature and effect on electrical impedance during radiofrequency ablation of ventricular myocardium"; Circulation, vol. 62, No. 3; Reference pp. 1034-1038; Publication Date: Sep. 1990.

Hoffmann, Ellen; "Biophysical parameters of radiofrequency catheter ablation"; Citation: International Journal of Cardiology, vol. 37; Reference pp. 213-222; Publication Date: Dec. 1992.

Horn, Berthold K.P.; "Closed-form solution of absolute orientation using unit quaternions"; Journal of teh Optical Society of America, vol. 4; Reference pp. 629-642; Publication Date: Apr. 1987.

Howie, Michael B.; "An Evaluation of a New Two-Electrode Myocardial Electrical Impedance Monitor for Detecting Myocardial Ischemia"; Anesth. Analg, vol. 92:12-8; Reference pp. 12-18; Publication Date: Jan. 2001.

Kearsley, Simon; "On the orthogonal transformation used for structural comparisons"; Acta Crystallographica Vo. A45, Reference pp. 208-210; Publication Date: Feb. 1989.

Ko, Wen-Chin, "New Method for Predicting Efficiency of Heating by Measuring Bioimpedance During Radiofrequency Catheter Ablation in Humans"; Journal of Cardiovascular Electrophysiology, vol. 12, No. 7; Reference pp. 819-823: Publication Date: Jul. 2001.

Lang, Christopher C.E.; "Endocardial impedance mapping during circumferential pulmonary vein ablation of atrial fibrillation differentiates between atrial and venous tissue"; Heart Rhythm Society, vol. 3, No. 2; Reference pp. 171-178; Publicaton Date: Feb. 2006.

Author: Orr, Mark J Title: Introduction to radial basis fuction networks Reference pp. 1-67 Publication Date: Apr. 1996.

Ragheb, T.; "The Impedance of a Spherical Monopolar Electrode"; Annals of Biomedical Engineering, vol. 20; Reference pp. 617-627; Publication Date: Nov. 1992.

(56) References Cited

OTHER PUBLICATIONS

Ragheb, T.; "The Polarization Impedance of Common Electrode Metals Operated at Low Current Density"; Annals of Biomedical Engineering, vol. 19, Issue 2; Reference pp. 151-163: Publication Date: Mar. 1991.

Salazar, Yolocuauhtli; "Effect of electrode locations and respiration in the characterization of myocardial tissue using a transcatheter impedance method"; Physiological Measurement, No. 25, Reference pp. 1095-1103: Publication Date: Oct. 2004.

Salazar, Yolocuauhtli; "Transmural Versus Nontransmural In Situ Electrical Impedance Spectrum for Healthy, Ischemic, and Healed Myocardium"; IEEE Transactions on Biomedical Engineering, vol. 51 No. 9; Reference pp. 1421-1427; Publication Date: Aug. 2004.

Schwartzman, David; "Electrical Impedance Properties of Normal and Chronically Infarcted Left Ventricular Myocardium"; Journal of Interventional Cardiac Electrophysiology, vol. 3; Reference pp. 213-224; Publication Date: Oct. 1999.

Strickberger, S. Adam; "Relation between impedance and endocardial contact during radiofrequency catheter ablation"; American Heart Journal, vol. 1298, No. 2; Reference pp. 226-229; Publication Date: Aug. 1994.

Wolf, Tamir; "Three-dimensional endocardial impedance mapping: a new approach for myocardial infarction assessment", AJP—Heart and Circulatory Physiology, vol. 280; Reference pp. 179-186; Publication Date: Jan. 2001.

Zheng, Xiangsheng; "Electrode Impedance: An Indicator of Electrode-Tissue Contact and Lesion Dimensions During Linear Ablation"; Journal of Interventional Cardiac Electrophysiology 4; Reference pp. 645-654; Publication Date: Dec. 2000.

Cases, O.; "In Vivo and In Situ Ischemic Tissue Characterization Using Electrical Impedance Spectroscopy"; Annals New York Academy of Sciences, vol. 873; Reference pp. 51-58; Publication Date: Apr. 1999.

Chui, Haill; "A new algorithm for non-rigid point matching"; IEEE Conference on Computer Vision and pattern, vol. 2; Reference pp. 44-51; Publication Date: Jun. 2000.

European Search Report in EP Application No. 09015744.7 (Jun. 4, 2010).

Ju, Tao; "Mean Value Coordinates for Closed Trangular Meshes"; ACM Transactions on Graphics 24(3); Reference pp. 561-566; Publication Date: Jul. 2005.

Wittkampf, Fred H.; "LocaLisa: New Technique for Real-Time 3-Dimensional localization of regular intracardiac electrodes"; Circulation—Journal of the American Heart Association; Reference pp. 1312-1317; Publication Date: Mar. 1999.

\* cited by examiner

DETERMINATION OF CARDIAC GEOMETRY RESPONSIVE TO DOPPLER BASED IMAGING OF BLOOD FLOW CHARACTERISTICS

BACKGROUND OF THE INVENTION a. Field of the Invention

This invention relates to a system and method for identifying physical structures in a body. In particular, the instant invention relates to a system and method that identify the location of physical structures based on fluid flow within the body as shown in images of the body.

b. Background Art

The flow of a fluid such as blood within a region of interest in a body can be detected and illustrated in images of the region. In particular, ultrasound transducers disposed within the cardiovascular system can detect a Doppler shift (or change in frequency and wavelength) in waves associated with the blood as it moves relative to the transducers. Using information from the transducers, an electronic control unit can generate image data used to illustrate the blood flow within the region. Within the image, the blood flow is often colored using predetermined colors depending on whether the blood is flowing towards or away from the transducers. Based on the illustrated flow of blood and its color, a clinician can often identify physical structures within the image. For example, with the transducer placed in the left atrium of the heart, blood flowing away from the transducer is indicative of blood flowing outward through the mitral valve and into the left ventricle. Similarly, blood flowing towards the transducer is indicative of blood flowing into the left atrium from the pulmonary veins. While existing technologies permit the clinician to estimate blood flow velocity and to confirm the identify of physical structures by viewing the direction, timing and speed of blood flow in the image, these technologies do not permit a precise identification of the location of a physical structure.

Blood flow is often detected and imaged through intracardiac echocardiography (ICE) using an ultrasound transducer disposed on a catheter threaded through the vasculature of the body. Some conventional systems can have attached optical or magnetic position and orientation sensors to the ICE catheter to enable registration of the image captured by the ICE catheter within the three dimensional coordinate system. The accuracy of registration is impacted by variations in the manufacture and implementation of the ICE catheter and the position and orientation sensors. In position and orientation sensing systems based on electric fields, there can also be instability and variations in the navigational potential field and the reference electrodes. Calibration of position and orientation sensors on the catheter is therefore necessary. Calibration of sensors based on electric fields is presently accomplished via registration to some other sensing technology, typically magnetic. Such registration requires manufacture of a catheter with both magnetic and electric field sensors. Consequently, there is utility in calibration of an electric-field sensor on an ICE catheter using information present in the ultrasound data.

The inventors herein have recognized a need for a system and method for identifying the location of physical structures in the body that will minimize and/or eliminate one or more of the above-identified deficiencies.

BRIEF SUMMARY OF THE INVENTION

It is desirable to provide a system and method for identifying a location of a physical structure in a body. In particular, it is desirable to provide a system and method in which the location of the physical structure can be precisely identified based on fluid flow shown within an image of a region of interest in the body.

A system for identifying a location of a physical structure in a body in accordance with one embodiment of the invention includes an electronic control unit configured to register a first image of a portion of the body in a three-dimensional coordinate system. The electronic control unit is further configured to identify the location of the physical structure in the three-dimensional coordinate system responsive to flow of a fluid shown in the image. In accordance with one embodiment of the invention, the electronic control unit is further configured to generate a second image incorporating a representation of the physical structure within a larger physical environment in the three-dimensional coordinate system. For example, the second image may comprise a three-dimensional model of a portion of the body such as an electroanatomical map of the heart including the physical structure.

A method for identifying a location of a physical structure in a body in accordance with one embodiment of the invention includes the step of registering a first image of a portion of the body in a three-dimensional coordinate system. The method also includes the step of identifying the location of the physical structure in the three-dimensional coordinate system responsive to flow of a fluid shown in the image.

A system and method in accordance with the present invention are advantageous because they allow precise identification of the location of a physical structure based on fluid flow. Based on information associated with fluid flow in the image, the location and size of key physical structures such as the mitral valve and pulmonary veins in the heart can be identified. Using this location and size information, improved representations of physical structures can be generated to allow clinicians a more accurate depiction of the physical geometry of the body and improved diagnostic assessment and therapeutic approaches.

The foregoing and other aspects, features, details, utilities and advantages of the present invention will be apparent from reading the following description and claims, and from reviewing the accompanying drawings.

DETAILED DESCRIPTION OF EMBODIMENTS OF THE INVENTION

Figure 1:
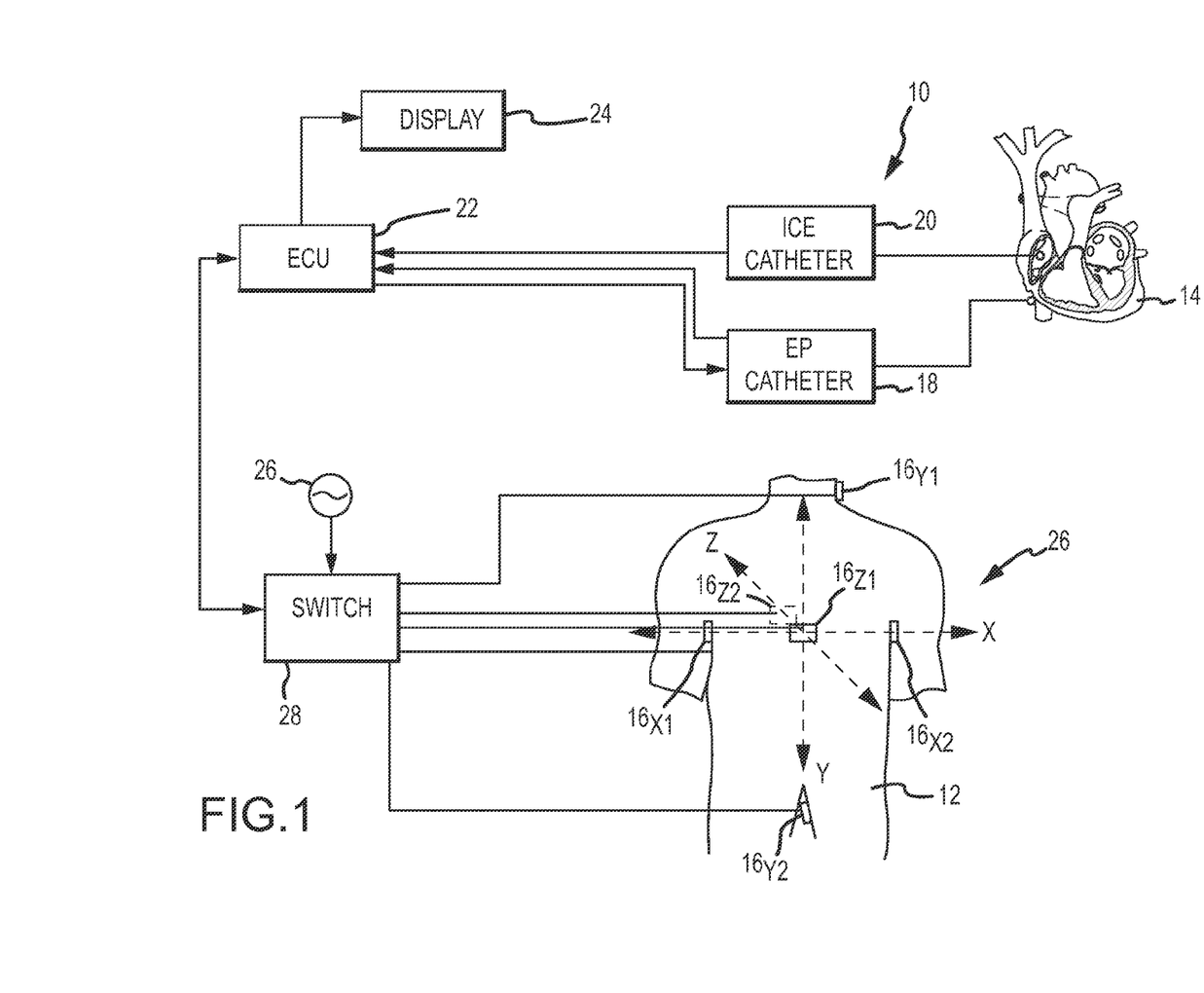
FIG. 1 is diagrammatic view of a system in accordance with the present teachings.

Referring now to the drawings wherein like reference numerals are used to identify identical components in the various views, FIG. 1 illustrates one embodiment of a system 10 for identifying the location of a physical structure in a body 12 and, in particular, the location of a physical structure in the heart 14 of a human body. System 10 may include a plurality of patch electrodes 16 applied to body 12, an electrophysiological (EP) catheter 18, an intracardiac electrocardiography (ICE) catheter 20, an electronic control unit (ECU) 22 and a display 24.

Patch electrodes 16 are provided to generate electrical signals used in determining the position of EP catheter 18 within a three dimensional coordinate system 26 and in generating EP data regarding heart 14. Electrodes 16 may also be used to determine the position of ICE catheter 20 within coordinate system 26 and related information. Electrodes 16 are placed orthogonally on the surface of body 12 and are used to create axes specific electric fields within body 12. Electrodes $16_{X1}$, $16_{X2}$ may be placed along a first (x) axis. Similarly, electrodes $16_{Y1}$, $16_{Y2}$ may be placed along a second (y) axis and electrodes $16_{Z1}$, $16_{Z2}$ may be placed along a third (z) axis. Each of the electrodes 16 may be coupled to a multiplex switch 28. ECU 22 is configured through appropriate software to provide control signals to switch 28 and thereby sequentially couple pairs of electrodes 16 to a signal generator 30. Excitation of each pair of electrodes 16 generates an electromagnetic field within body 12 and within an area of interest such as heart 14. Voltage levels at non-excited electrodes 16 are filtered and converted and provided to ECU 22 for use as reference values.

EP catheter 18 is provided for use in gathering EP data associated with heart 14 to enable generation of an image of the geometry of the heart surface and related EP data. Catheter 18 may also allow removal of bodily fluids or injection of fluids and medicine into the body and may further provide a means for transporting surgical tools or instruments within a body including those use for pacing or tissue ablation. Catheter 18 may be formed from conventional materials such as polyurethane. Catheter 18 is tubular and is deformable and may be guided within a body by a guide wire or other means known in the art. Catheter 18 has a proximal end and a distal end. As used herein, "distal" refers to an end of catheter 18 that is advanced to the region of interest within body 12 while "proximal" refers to the opposite end of catheter 18 that is disposed outside of the body and manipulated manually by a clinician or automatically through, for example, robotic controls. Catheter 18 may be inserted within a vessel located near the surface of a body (e.g., in an artery or vein in the leg, neck, or arm) in a conventional manner and maneuvered to a region of interest in body 12 such as heart 14.

Figure 2:
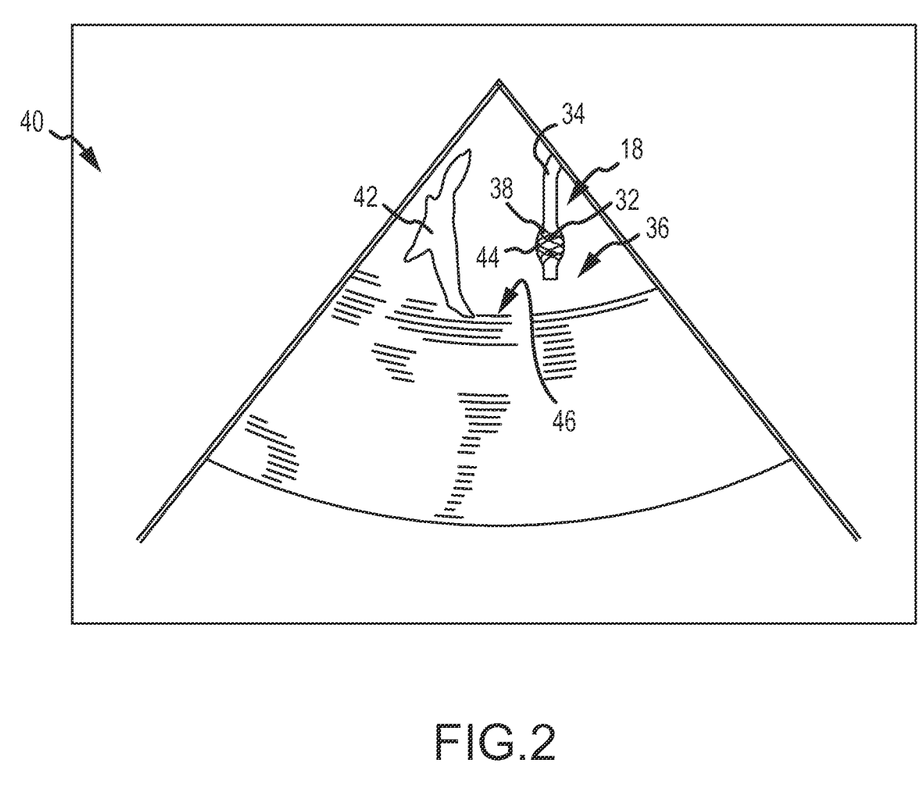
FIG. 2 is a diagrammatic representation of an intracardiac echocardiograph (ICE) image showing blood flow within a portion of the heart.

Referring to FIG. 2, EP catheter 18 includes a plurality of EP mapping electrodes 32. The electrodes 32 are placed within electrical fields created in body 12 (e.g., within the heart 14) by exciting patch electrodes 16. The electrodes 32 experience voltages that are dependent on the location between the patch electrodes 16 and the position of the electrodes 32 relative to the surface of heart 14. Voltage measurement comparisons made between electrodes 32 can be used to determine the position of the electrodes 32 within heart 14. Movement of the electrodes 32 within heart 14 (e.g., within a heart chamber) produces information regarding the geometry of the heart 14 as well as EP data. For example, voltage levels on the tissue surface over time may be projected on the image of the geometry of the heart as an activation map. The voltage levels may be represented in various colors and the EP data may be animated to show the passage of electromagnetic waves over the tissue surface. Information received from the electrodes 32 can also be used to display the location and orientation of the electrodes 32 and/or the tip of EP catheter 18 within heart 14.

EP catheter 18 is preferably a non-contact mapping catheter such as the catheter sold by St. Jude Medical, Atrial Fibrillation Division, Inc. under the registered trademark "ENSITE ARRAY." It should be understood, however, that the present invention may also be used with contact mapping systems in which measurements are taken through contact of the electrodes with the tissue surface. Referring to FIG. 2, catheter 18 includes a deformable tubular body 34 including a deformable distal portion 36. Portion 36 may be formed as a braid of insulated wires 38 with an array of electrodes 32 formed where the insulation on the wires 38 has been removed. Portion 36 may be deformed by expansion (e.g. through use of a balloon) into a stable and reproducible geometric shape to fill a space (e.g., a portion of a heart chamber) after introduction into the space. One or more reference electrodes (not shown) may also be located nearer the distal end of catheter 18 than electrodes 32 and may contact the tissue surface to calibrate the electrode array and maintain the position of the electrode array. An exemplary EP catheter is shown in commonly assigned U.S. Pat. No. 7,289,843, the entire disclosure of which is incorporated herein by reference.

Referring again to FIG. 1, ICE catheter 20 is used to generate an image of a region of interest within body 12 such as heart 14. Catheter 20 may, for example, comprise one of the catheters sold by St. Jude Medical, Atrial Fibrillation Division, Inc. under the registered trademark "VIEWFLEX." Like catheter 18, catheter 20 may be formed from conventional materials such as polyurethane. Catheter 20 is tubular and is deformable and may be guided within a body by a guide wire or other means known in the art. Catheter 20 has a proximal end and a distal end. As used herein, "distal" refers to an end of catheter 20 that is advanced to the region of interest within body 12 while "proximal" refers to the opposite end of catheter 20 that is disposed outside of the body and manipulated manually by a clinician or automatically through, for example, robotic controls. Catheter 20 may be inserted within a vessel located near the surface of a body (e.g., in an artery or vein in the leg, neck, or arm) in a conventional manner and maneuvered to a region of interest in body 12 such as heart 14. Catheter 20 includes one or more ultrasound transducers used to emit ultrasound signals within heart 14 and/or to receive reflected ultrasound signals from physical structures within heart 14 such as chamber and vascular walls and fluids flowing within heart 14. Catheter 20 may generate ultrasound signals from transducers under the control of ECU 22 and generates return signals to ECU 22 responsive to the reflected ultrasound signals for use in creating an image 40 of the internal geometry of the heart 14 as shown in FIG. 2. Catheter 20 may include means, such as one or more position sensors, for determining the position and orientation of catheter 20 within a coordinate system such as coordinate system 26. A variety of conventional position sensors could be used including electrodes that work in a manner similar to electrodes 32 in EP catheter 18—generating signals responsive to excitation of patch electrodes 16 that permit ECU 22 to determine the location of catheter 20. It should also be understood, however, that other conventional position sensing systems could be used including magnetic positioning systems such as the system sold under the trademark "GMPS" by Mediguide, Ltd. or the system sold under the trademark "CARTO" by Biosense Webster, Inc. in which the case the position sensors comprise magnetic sensors such as coils.

Referring again to FIG. 2, an image 40 generated from data obtained by ICE catheter 20 is shown. Image 40 may be generated on display 24 responsive to signals from ECU 22. Image 40 may comprise a two dimensional image of a portion of body 12 such as a portion of heart 14. In the illustrated embodiment, image 40 shows a portion of the left atrium of the heart. In accordance with certain embodiments, image 40 illustrates the flow of fluid within body 12 such as the flow of blood within heart 14. Transducers on ICE catheter 20 detect a Doppler shift (or change in frequency and wavelength) in waves associated with the blood as it moves relative to the transducers. Using information from the transducers, ECU 22 generates image data such that image 40 illustrate the blood flow within heart 14. Within the illustrated embodiment, the flow of blood is illustrated as a plume 42 emanating from a fluid source such as a pulmonary vein in the left atrium of heart 14. In accordance with conventional practice, plume 42 is preferably colored using a predetermined color scheme to indicate whether the blood is flowing towards or away from the transducers (e.g. red for blood moving towards the transducers such as when blood is entering a heart chamber and blue for blood moving away from the transducers such as when blood is exiting the chamber).

In accordance with embodiments of the invention, image 40 also captures one or more fiducial markers 44 that are used to register the image within coordinate system 26 as described hereinbelow. The markers 44 either comprise, or are located at predetermined offsets from, one or more position sensors whose position and orientation within coordinate system 26 is determined by ECU 22 responsive to signals generated by the position sensors responsive to excitation of patch electrodes 16. In the illustrated embodiment, markers 44 comprise position sensors and, in particular, electrodes 32 on EP catheter 18, the distal end 36 of which may be positioned within the left atrium of heart 14 using a conventional transseptal approach. Markers 44 may also comprise position sensors mounted on devices other than EP catheter 18. For example, markers 44 could comprise position sensors such as conventional tip or ring electrodes located on diagnostic or therapeutic devices such as a conventional ablation catheter. Markers 44 could also comprise position sensors (including again, for example, electrodes) located on a catheter or another device whose sole or primary purpose is to provide the markers 44 as a reference point for registration of image 40 within coordinate system 26. As noted above, markers 44 need not comprise position sensors, but may be located a predetermined offset from position sensors thereby allowing ECU to determined the position of markers 44 within coordinate system 26 based on the coordinates of the position sensors. Although image 40 can be registered in coordinate system responsive to the position of a single position sensor in coordinate system 26 and image 40 by simple translation, increased precision is obtained by registering image 40 responsive to the position of multiple position sensors. For example, the use of three position sensors (either as fiducial markers 44 or as references for one or more markers 44) will provide six degrees of freedom position sensing that permits orientation and scaling adjustments such that the position and orientation of markers 44 along each axis of three orthogonal axes is known. Finally, although the above-described embodiments generally describe determining the position of markers 44 based on electromagnetic fields generated through patch electrodes 16, it should be understood that the number or position of markers 44 could be determined using a variety of position sensing systems by selecting appropriate forms of position sensors and position detection systems. For example, magnetic position sensors could be used in a magnetic positioning systems such as the system offered for sale under the trademark "GMPS" by Mediguide Ltd. to identify the position of markers 44 within a coordinate system of the magnetic position sensing system.

Electronic control unit (ECU) 22 provides a means for controlling the operation of various components of system 10 including EP catheter 18, ICE catheter 20 and switch 28. ECU 22 also provides a means for determining the geometry of tissue 12, EP characteristics of tissue 12 and the position and orientation of EP catheter 18 and ICE catheter 20 and fiducial markers 44. ECU 22 also provides a means for generating display signals used to control display 24. ECU 22 may comprise a programmable microprocessor or microcontroller or may comprise an application specific integrated circuit (ASIC). ECU 22 may include a central processing unit (CPU) and an input/output (I/O) interface through which ECU 22 may receive a plurality of input signals including signals generated by patch electrodes 16, EP catheter 18 (and mapping electrodes 32), ICE catheter 20 and positions sensors located on EP catheter 18, ICE catheter 20 or other devices and generate a plurality of output signals including those used to control and/or provide data to EP catheter 18, ICE catheter 20, display 24, and switch 28.

In operation, ECU 22 generates signals to control switch 26 and thereby selectively energize patch electrodes 16. ECU 22 receives position signals from EP catheter 18 (and particularly mapping electrodes 32) reflecting changes in voltage levels on mapping electrodes 32 and from the non-energized patch electrodes 16. ECU 22 uses the raw location data produced by electrodes 16, 32 and corrects the data to account for respiration and other artifacts. ECU 22 then generates display signals to create an electrophysiological map of heart 14. ECU 22 also receives signals generated by transducers on ICE catheter 20 and uses the information contained in these signals to generate image 40.

In accordance with the present teachings, ECU 22 is configured to perform several steps in a method for identifying a location of a physical structure in body 12. ECU may be configured to register image 40 in a three-dimensional coordinate system such as coordinate system 26 responsive to a position of one or more fiducial markers 44 in image 40 and a position of a position sensor with which the fiducial markers are associated in the coordinate system 26. Because the location of the position sensor within coordinate system 26 is known and markers 44 have a known positional relationship relative to the sensor, ECU 22 can register image 40 within coordinate system 26 by reference to markers 44. The position information obtained from markers 44 in image 40 can be used alone to register image 40 or it can be used in combination with other information that permits registration of image 40 including, for example, information derived from a position sensor on ICE catheter 20. For example, the information derived from these two sources can be weighted to various degrees and coordinates determined using Bayesian probability techniques and a Procrustes least squares approach can be used to align the information derived from the two sources through translation and rotation. In the case where registration of image 40 is accomplished using information from markers 44 in image 40 and information from another source as a position sensor on ICE catheter 20, steps may be taken to insure that the resulting registration coordinates are aligned with coordinate system 26. For example, ECU 22 may correct for known anatomic distortions in body 12. The position sensors may also be located as near as possible to region of interest. Multiple electrodes may also be used to compensate for field distortion including, for example, the multi-electrode catheter disclosed in pending and commonly assigned U.S. patent application Ser. No. 12/346,592, the entire disclosure of which is incorporated herein by reference. It should be understood that image 40 can be registered in coordinate system 26 or, alternatively, in another coordinate system by translation and scaling of positional coordinates for one or both of image 40 and the position sensor. ECU 22 may be further configured to register image 40 with another image of a portion of body 12, such as heart 14 using, for example, the same markers 44 in each image.

Figure 3:
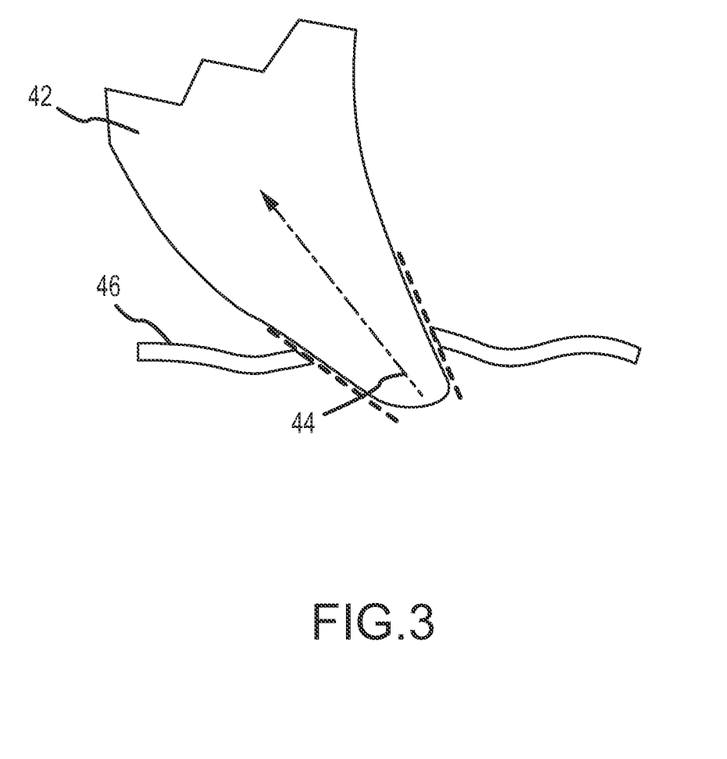
FIG. 3 is a diagrammatic representation of a portion of an intracardiac echocardiograph (ICE) image showing blood flow within a portion of the heart.

ECU 22 is further configured to identify the location of a physical structure in coordinate system 26 responsive to flow of a fluid shown in image 40. Having registered image 40 within coordinate system 26 on the basis of the position of fiducial markers 44, ECU 22 can locate the position of other structures or features shown in image 40 within coordinate system 26. As discussed hereinabove, characteristics associated with fluid flow in ultrasound images can be used to identify physical structures within a body. For example, within the left atrium of the heart, blood flowing away from an ultrasound transducer may be have one color in image 40 and is indicative of blood flowing outward through the mitral valve and into the left ventricle. Similarly, blood flowing towards the transducer may have another color in image 40 and is indicative of blood flowing into the left atrium from the pulmonary veins. The color of plume 42 within image 40 and/or the data on which the assignment of color was based such as fluid flow velocity and phase of the cardiac cycle may therefore be used by ECU 22 to identify a physical structure and—based on the prior registration of image 40 in coordinate system 26—the particular location of the structure within coordinate system 26. For example, for an ultrasound transducer in the left atrium, fluid flow velocity away from the transducer of between 0.2 meters per second and 2.0 meters per second in early and late diastole is indicative of fluid flow exiting the left atrium through the mitral valve. Lower fluid flow velocities towards the transducer are indicative of fluid flow into the left atrium from the pulmonary veins. Referring to FIG. 3, the shape of plume 42 in image 40 can also be used by ECU 22 to identify and, consequently, locate physical structures in body 12. In particular, the shape of plume 42 can be used by ECU 22 to approximate the velocity vector 44 of the blood flow. Using this information and conventional edge detection techniques to locate the atrial wall 46 in image 40, ECU 22 can identify the location of the pulmonary vein ostium or mitral valve orifice including the diameter of the ostium or orifice and the location of the edges of the ostium or orifice. In the above-described embodiment, a single image 40 is registered in coordinate system 26 and the location of a physical structure in coordinate system 26 is identified using information associated with image 40. It should be understood that ECU 22 can be further configured to register a plurality of images in coordinate system 26 (e.g. from different viewpoints) and to identify the location of the physical structure using information associated with the plurality of images.

Figure 4:
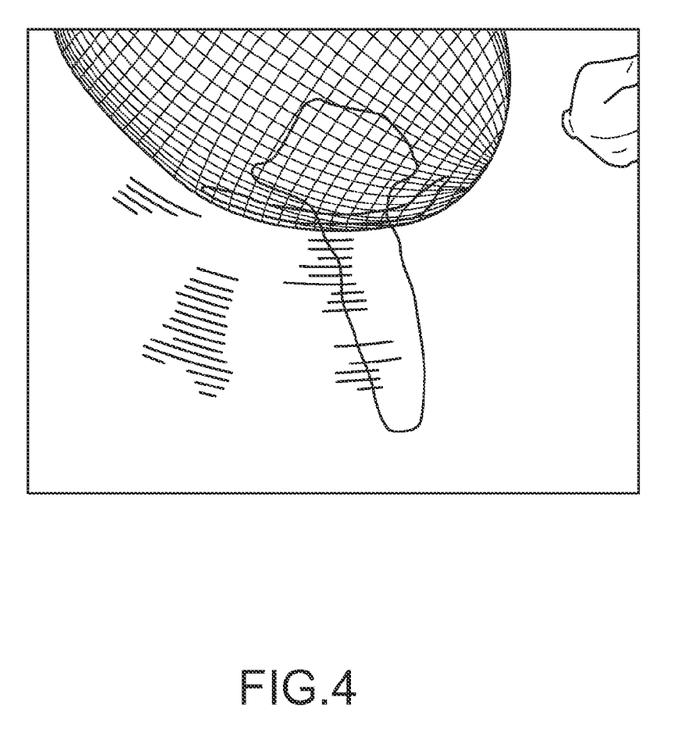
FIG. 4 is a diagrammatic representation of an image showing a three-dimensional model of the heart contrasted with an ICE image showing blood flow within the heart.

In accordance with various embodiments of the invention, ECU 22 is also configured to generate an image incorporating a representation of the identified physical structure within a larger physical environment in coordinate system 26. In one embodiment of the invention, the image may comprise a three dimensional model of the physical environment and/or an electroanatomical map of the physical environment. In one particular embodiment, the physical environment comprises the heart or a portion thereof and the physical structure that is represented in the environment is a pulmonary vein and/or its ostium or a mitral valve and/or the orifice of the mitral valve. Referring to FIG. 4, ECU 22 generates the image of the physical environment in accordance with conventional mapping and image generating techniques. For example, electrodes 32 at one end of catheter 18 may be moved within the heart chambers by the clinician while the heart is beating. The locations of the catheter electrodes 32 are measured, for example, using patch electrodes 16 or another sensor (e.g., a magnetic sensor (not shown)) and stored by ECU 22 as a "cloud" of points. A conventional algorithm such as a convex hull algorithm is used to construct a surface around the cloud. The most exterior points are used to create a "shell" representing the shape of the heart. Additional sampling and smoothing operations are then performed to generate the anatomical map as shown in FIG. 4. A more detailed explanation of the mapping process is described in the above-referenced U.S. Pat. No. 7,263,397 titled "Method and Apparatus for Catheter Navigation and Location and Mapping in the Heart," the entire disclosure of which is incorporated herein by reference.

Figure 5A:
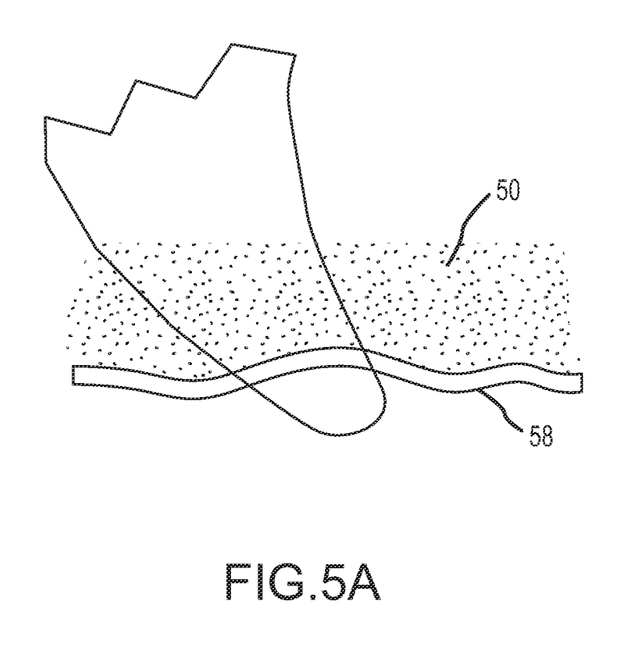
FIGS. 5A and 5B are diagrammatic representations of the conversion of image information to points in a point cloud.
Figure 5B:
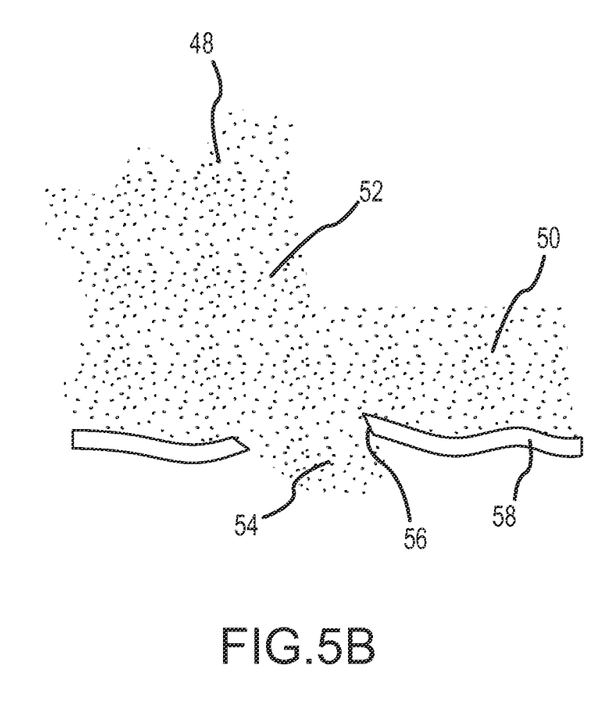
Figure 6A:
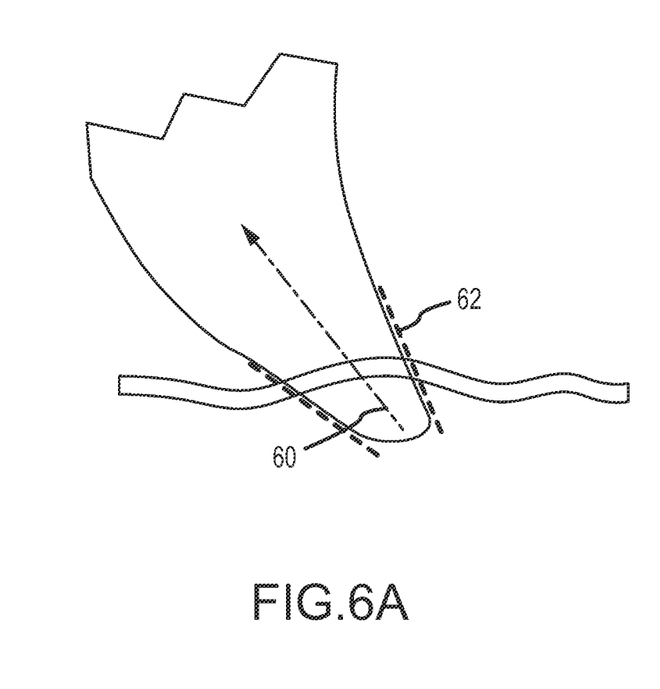
FIGS. 6A and 6B are diagrammatic representations illustrating the identification and creation of physical structure in an image based on fluid flow.
Figure 6B:
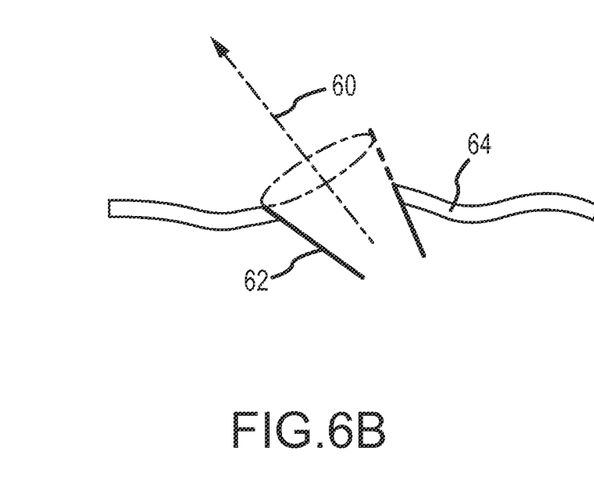
Figure 7:
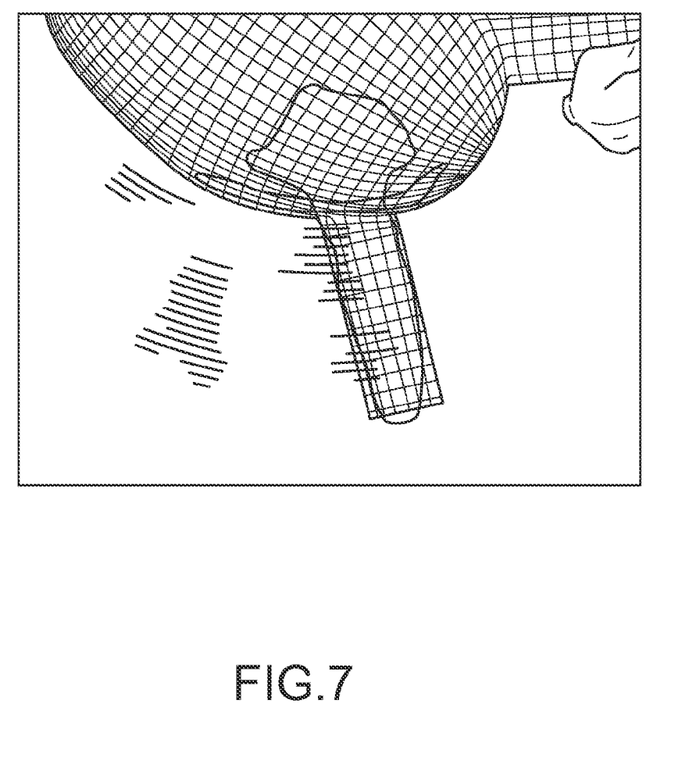
FIG. 7 is a diagrammatic representation of an image showing a three-dimensional model of the heart and additional physical structure obtained using the a system in accordance with the present teachings.

By virtue of the process used to create the map or model, each point in the physical environment shown in the map or model is located within the coordinate system 26. Having identified and located a physical structure based on registration of image 40 and use of fluid flow information, ECU 22 is capable of representing the structure within the image of the physical environment at a precise location relative to other structures within the environment. Referring to FIGS. 5A and 5B, in accordance with one embodiment of the invention ECU 22 generates this image in part by adding points 48 corresponding to the location of the physical structure to the point cloud 50 corresponding to the physical environment. In particular, ECU 22 may add points 48 corresponding to the flow of the fluid in image 40 to the point cloud 50 corresponding to the physical environment. The added points may correspond to only the border of the fluid shown in image 40, but may also include points corresponding to points in image 40 within the border. In either case, as shown in FIGS. 5A and 5B, the addition of these points can help identify the location of physical structures such as intracardiac space 52 or intravascular space 54 (wherever blood flow is indicated by definition must comprise space) and the pulmonary vein ostium 56 or mitral valve orifice in the atrial wall 58. Referring to FIGS. 6A and 6B, for example, manual or automated processes can be used to identify the centroid and major axis 60 of the fluid flow representation and assign a direction the flow. Using the most distal portion of the flow, edges 62 of the flow can be created that are aligned with the axis 62 and taper appropriately. Edges 62 approximate the surface of a vessel such as a pulmonary vein ostium. The image can be adjusted to account for edges 62 by, for example interrupting the atrial wall 64 between edges 62. Different colors can be used to represent edges 62 and wall 64 to aid the clinician in visualizing the structures. Referring to FIG. 7, ECU 22 can—using the above-described techniques—generate an image incorporating a representation of the identified physical structure within a larger physical environment previously shown in FIG. 4.

In accordance with another aspect of the present invention, ECU 22 may be further configured to register the map or model with a preacquired imaged such as a segmented magnetic resonance (MR) or computed tomography (CT) image. By matching distinctive physical structures such as the pulmonary vein ostia shown in the man/model and preacquired image, ECU 22 is capable of registering the map/model and preacquired image. Similarly, ECU 22 can perform the registration based on characteristics shown in the map/model and image such as the location and/or direction of fluid flow.

Display 24 is provided to convey information to a physician to assist in diagnosis and treatment. Display 24 may comprise a conventional computer monitor or other display device. Display 24 presents a graphical user interface (GUI) to the physician. The GUI may include a variety of information including, for example, an image of the geometry of heart 14, EP data associated with heart 14, graphs illustrating voltage levels over time for various electrodes, and images of EP catheter 18 and mapping electrodes 32. Examples of the type of information that may be displayed are shown in commonly assigned U.S. Pat. No. 7,263,397, the entire disclosure of which is incorporated herein by reference.

In practice, a method of diagnosis or treatment in accordance with the present invention may include several steps. First, an image 40 of a portion of body 12 is registered in a three-dimensional coordinate system such as coordinate system 26 responsive to a position of a fiducial marker 44 in the image 40 and the position of a position sensor associated with marker 44 in coordinate system 26. This step may include the substep of determining the position of the sensor within coordinate system 26. In one embodiment of the invention, the position may be determined by exciting electrodes 16 under the control of ECU 22 to create electromagnetic fields within body 12 and detecting the voltage levels present on an electrode 32 serving as the sensor. Because the fiducial marker 44 is associated with the sensor and has a known positional relationship relative to the sensor and because the position of the sensor within coordinate system 26 is known, image 40 may be registered within coordinate system 26. The method further includes the step of identifying a location of a physical structure in coordinate system 26 responsive to flow of a fluid shown in image 40. As discussed hereinabove, the illustrated fluid flow in image 40 (including, e.g., the color) and/or the data used to generate the illustrated fluid flow (e.g., velocity flow data, the phase of the cardiac cycle) can be used to both identify and locate a particular physical structure. The method may further include the step of generating an image incorporating a representation of the physical structure within a larger physical environment in coordinate system 26. As discussed hereinabove, the location information associated with the structure enables ECU 22 to integrate the structure into the broader physical environment obtained by, for example, EP catheter 18.

A system and method for identifying the location of a physical structure in a body in accordance with the present invention are advantageous because they allow precise identification of the location of a physical structure based on fluid flow. Based on information associated with fluid flow in the image, the location and size of key physical structures such as the mitral valve and pulmonary veins can be identified. Using this location and size information, improved representations of physical structures can be generated to allow clinicians a more accurate depiction of the physical geometry of the body and improved diagnostic assessment and therapeutic approaches. For example, a clinician performing a cardiac ablation procedure can guide and place an ablation catheter or other intravascular tool more accurately than in conventional systems—particularly near the pulmonary veins. In another example, the contribution of each pulmonary vein to blood flow and cardiac output can be determined using flow measurements and the size of the pulmonary vein ostia as determined by the invention.

Although several embodiments of this invention have been described above with a certain degree of particularity, those skilled in the art could make numerous alterations to the disclosed embodiments without departing from the scope of this invention. All directional references (e.g., upper, lower, upward, downward, left, right, leftward, rightward, top, bottom, above, below, vertical, horizontal, clockwise and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims.

What is claimed is:

1. A system for identifying a location of a physical structure in a body, comprising:
    an electronic control unit configured to:
        register a first echocardiography image of a portion of said body in a three-dimensional coordinate system responsive to a position of a fiducial marker in said first image and a position of a first sensor in said three-dimensional coordinate system, said sensor associated with said fiducial marker;
        identify said location of said physical structure in said three-dimensional coordinate system responsive to flow of a fluid shown in said image; and
        add points corresponding to said location of said physical structure to a point cloud corresponding to said physical environment, said point cloud comprising points collected with said sensor.

2. The system of claim 1 wherein said first image is an intracardiac echocardiography image.

3. The system of claim 1 wherein said physical structure comprises a pulmonary vein.

4. The system of claim 1 wherein said physical structure comprises a orifice of a mitral valve.

5. The system of claim 1 wherein said physical structure comprises an intracardiac or intravascular space.

6. The system of claim 1 wherein said fiducial marker is said first sensor.

7. The system of claim 1 wherein said fiducial marker is positioned at a predetermined offset from said first sensor.

8. The system of claim 1 wherein said first sensor comprises an electrode.

9. The system of claim 1 wherein said first sensor comprises a coil.

10. The system of claim 1 wherein said first image is registered responsive to said position of said fiducial marker in said first image and positions of a plurality of sensors in said three-dimensional coordinate system, said plurality of sensors associated with said fiducial marker.

11. The system of claim 10 wherein said plurality of sensors establish a position and an orientation of said fiducial marker along each of three axes, each axis of said three axes orthogonal to the other two axes of said three axes.

12. The system of claim 1 wherein said electronic control unit is further configured to identify said physical structure responsive to a phase of a cardiac cycle.

13. The system of claim 1 wherein said electronic control unit is further configured to generate a second image incorporating a representation of said physical structure within a larger physical environment in said three-dimensional coordinate system.

14. The system of claim 13 wherein said electronic control unit is further configured to add points corresponding to said flow of said fluid to said point cloud.

15. The system of claim 14 wherein said points correspond to a border of said fluid in said first image.

16. The system of claim 13 wherein said second image comprises a three-dimensional model of said physical environment.

17. The system of claim 13 wherein said second image comprises an electroanatomical map of said physical environment.

18. A method for identifying a location of a physical structure in a body, comprising:
executing a plurality of program instructions in an electronic control unit including instructions for:
determining a position of a fiducial marker in a first image of a portion of a body and a position of a first sensor in a three-dimensional coordinate system, said sensor associated with said fiducial marker;
registering the first image in said three-dimensional coordinate system;
identifying said location of said physical structure in said three-dimensional coordinate system responsive to flow of a fluid in said image;
adding points corresponding to said location of said physical structure to a point cloud corresponding to said physical environment, said point cloud comprising points collected with said sensor.

19. The method of claim 18 wherein said fiducial marker is said first sensor.

20. The method of claim 18 wherein said plurality of program instructions including instructions for registering said first image with a second image of said portion of said body.

21. The method of claim 18 wherein said plurality of program instructions including instructions for generating a second image incorporating a representation of said physical structure within a larger physical environment in said three-dimensional coordinate system.

22. The system of claim 1 wherein an origin of said three-dimensional coordinate system is not associated with said first image.

23. The system of claim 1 wherein an origin of said three-dimensional coordinate system is associated with a medical device position sensing system.

* * * * *

UNITED STATES PATENT AND TRADEMARK OFFICE
CERTIFICATE OF CORRECTION

PATENT NO.        : 8,948,476 B2
APPLICATION NO.   : 12/972723
DATED             : February 3, 2015
INVENTOR(S)       : D. Curtis Deno et al.

Page 1 of 1

It is certified that error appears in the above-identified patent and that said Letters Patent is hereby corrected as shown below:

Claims

Column 11, claim 18, line 21, kindly delete "image;" and replace with --image; and--.

Signed and Sealed this
Seventeenth Day of November, 2015

Michelle K. Lee
*Director of the United States Patent and Trademark Office*